(12) United States Patent
Sherman

(10) Patent No.: US 9,932,133 B2
(45) Date of Patent: Apr. 3, 2018

(54) THERAPEUTIC JEWELRY

(71) Applicant: Hot Girls Pearls Inc., New York, NY (US)

(72) Inventor: Constance Sherman, New York, NY (US)

(73) Assignee: Hot Girls Pearls Inc., New York, NY (US)

( * ) Notice: Subject to any disclaimer, the term of this patent is extended or adjusted under 35 U.S.C. 154(b) by 411 days.

(21) Appl. No.: 14/604,402

(22) Filed: Jan. 23, 2015

(65) Prior Publication Data
US 2016/0213508 A1 Jul. 28, 2016

(51) Int. Cl.
*A44C 23/00* (2006.01)
*B65B 7/28* (2006.01)
(Continued)

(52) U.S. Cl.
CPC .......... *B65B 7/2821* (2013.01); *A44C 11/002* (2013.01); *A44C 15/00* (2013.01);
(Continued)

(58) Field of Classification Search
CPC ..... A44C 15/002; A44C 11/002; A44C 15/00; A44C 5/0023; A44C 15/003; A44C 23/00;
(Continued)

(56) References Cited

U.S. PATENT DOCUMENTS

| 5,265,669 | A | | 11/1993 | Schneider | |
|---|---|---|---|---|---|
| 5,409,500 | A | * | 4/1995 | Dyrek | A61F 7/10 607/111 |

(Continued)

OTHER PUBLICATIONS

Constance, www.thegrommet.com, published on Oct. 6, 2013 (Oct. 6, 2013), retrieved on Mar. 18, 2016 (Mar. 18, 2016), access at <https://web.archieve.org/web/20131006013458/http://www.grommet.com/hot-girls-pearls-body-cooling-jewelry>, entire document, especially video.

(Continued)

*Primary Examiner* — Kaitlyn Smith
*Assistant Examiner* — Yasamin Ekrami
(74) *Attorney, Agent, or Firm* — Dorsey & Whitney LLP

(57) ABSTRACT

Therapeutic jewelry is provided that can provide a therapeutic heating or cooling effect to a user. The therapeutic jewelry includes a thread, a first therapeutic container portion, a second therapeutic container portion, and a cap. The first therapeutic container portion defines a first internal cavity, includes a receiving member extending across, and has a hollow interior open at opposite sides of the first therapeutic portion to receive the thread there through. The second therapeutic container portion defines a second internal cavity and is connectable to the first container portion forming a jewelry element body such that the first and second internal cavities cooperatively form an interior fluid cavity. At least one of the first or second container portions define a filling aperture open to the interior fluid cavity of the jewelry element body, enabling filling the interior fluid cavity. The cap is operably connectable to seal the filling opening so that the interior fluid cavity is sealed to fluid therein, while maintaining the opening of the hollow interior of the receiving member open to receive the support device.

24 Claims, 3 Drawing Sheets

(51) Int. Cl.
*A61F 7/08* (2006.01)
*A44C 15/00* (2006.01)
*A44C 11/00* (2006.01)
*A61F 7/00* (2006.01)
*A61F 7/02* (2006.01)

(52) U.S. Cl.
CPC .......... *A61F 7/08* (2013.01); *A61F 2007/0011* (2013.01); *A61F 2007/0035* (2013.01); *A61F 2007/0098* (2013.01); *A61F 2007/0219* (2013.01); *A61F 2007/0268* (2013.01)

(58) Field of Classification Search
CPC ...... A61F 2007/0269; A61F 2007/0268; A61F 2007/0098; A61F 2007/0035; A61F 2007/0011; A45F 3/16; B65D 2517/0049; B65D 11/04; B65B 7/2821
See application file for complete search history.

(56) References Cited

U.S. PATENT DOCUMENTS

| | | | | |
|---|---|---|---|---|
| 6,221,245 | B1* | 4/2001 | Colburn | C02F 1/481 210/137 |
| 8,082,753 | B1* | 12/2011 | Alvarez, Jr. | A45F 3/16 224/148.1 |
| D672,465 | S* | 12/2012 | Sherman | D24/207 |
| 9,149,808 | B1* | 10/2015 | Smith | A45F 3/18 |
| 2003/0110549 | A1 | 6/2003 | Yeager | |
| 2009/0089988 | A1* | 4/2009 | Johnson, Sr. | A44C 23/00 27/1 |
| 2011/0127293 | A1 | 6/2011 | Pascatore | |
| 2012/0138637 | A1 | 6/2012 | Ciavarella et al. | |
| 2014/0358206 | A1* | 12/2014 | Hirokane | A61F 7/03 607/109 |

OTHER PUBLICATIONS

Constance Sherman, www.hotgirlspeals.com, published on Dec. 20, 2014 (Dec. 20, 2014), retrieved on Mar. 18, 2016 (Mar. 18, 2016), accessed at <https://web.archieve.org/web/20141220171720/http://www.hotgirlspearls.com/aboutus.html>, entire document.

International Search Report for International Application No. PCT/US2016/014608 dated Apr. 22, 2016.

The Beading Gem, www.thebeadinggem.com, published on Dec. 22, 2014 (Dec. 22, 2014), retrieved on Mar. 18, 2016 (Mar. 18, 2016), accessed at <https://web.archieve.org/web/2014222175250/http://www.thebeadinggem.com/2013/02/hot-girls-pears-menopause-necklaces.html>, entire document.

* cited by examiner

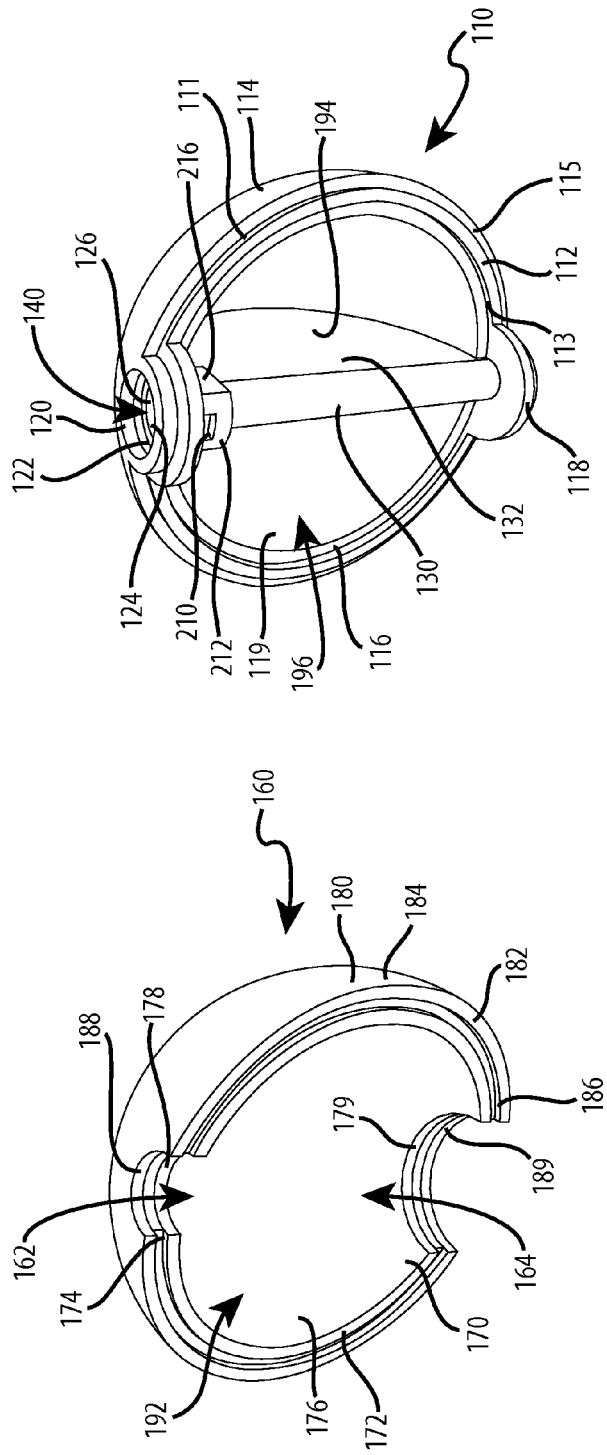

THERAPEUTIC JEWELRY

TECHNICAL FIELD

The present disclosure relates generally to therapeutic jewelry, and specifically to a device that is wearable by its user and provides a therapeutic heating or cooling effect.

BACKGROUND

Strung, costume pearls are known containing cooling gel, which are typically used by women in counteracting hot flashes, some women opt to use ice to cool themselves. Such known pearls, have included a plastic hemisphere that is filled with cooling gel, and then attached to another hemisphere to seal in the gel and form the pearl. As such, up to about half of the interior volume of the pearl is filled with gel. A passage is provided across the pearl's interior to accept a string connecting a string of pearls. An example of a known pearl construction is shown in U.S. Design Pat. No. 672,465. Improvements are needed in the construction of jewelry.

SUMMARY

Disclosed herein are various embodiments of a therapeutic jewelry device. In accordance with various embodiments, the therapeutic jewelry device may include a stringing member. The therapeutic jewelry device may also include a first therapeutic container portion. The first therapeutic container portion may define a first internal cavity. The first therapeutic container portion may include a receiving member extending across the first therapeutic container portion. The receiving member may include a hollow interior open at opposite sides of the first therapeutic portion. The hollow interior may receive the stringing member there through. The therapeutic jewelry device may also include a second therapeutic container portion. The second therapeutic container portion may define a second internal cavity. The first therapeutic container portion and the second therapeutic container portion may be connectable to one another thereby forming a jewelry element body. The first and second internal cavities may cooperatively form an interior fluid cavity. At least one of the first or second container portions may define a filling aperture open to the interior fluid cavity of the jewelry element body. The filling aperture may enable filling the interior fluid cavity. The therapeutic jewelry device may also include a cap that is operably connectable to seal the filling opening so that the interior fluid cavity is sealed to fluid therein while maintaining the opening of the hollow interior of the receiving member open to receive the stringing member.

In accordance with various embodiments, the receiving member may be a tubular channel that extends across the first therapeutic container portion. The filling aperture may be located within the hollow interior of the receiving member so that the interior fluid cavity is fillable through said hollow interior. The filling aperture may be at least one of a generally radial or a generally rectangular passage to the hollow interior fluid cavity. The hollow interior may include an enlarged portion near one of the openings. The filling aperture may be disposed in the enlarged portion. The enlarged portion may be operable to receive the cap such that the cap plugs the filling aperture located within the enlarged portion. The first therapeutic container portion, the second therapeutic container portion, or the cap may be plastic welded or adhered to one another. The cap may include a central through hole aligned with the hollow interior to receive the stringing member.

In accordance with various embodiments, the first therapeutic container portion and the second therapeutic container portion may be individual hemispheres that, when connected together, form a sphere. The receiving member and the cap through hole may be centered on a hemispherical surface of the second therapeutic container portion. The second therapeutic container portion may include a ridge extending from the hemispherical surface forming a tongue for engagement with the first therapeutic container portion. The first therapeutic container portion may include a groove extending into a hemispherical surface for receiving the tongue of the second therapeutic container and providing engagement there between.

In accordance with various embodiments, the first therapeutic container portion and the second therapeutic container portion may be connected together and filled with therapeutic fluid. The cap may be inserted into the hollow interior. The cap may be inserted into the enlarged portion positioned within the hollow interior. The cap may enclose the therapeutic fluid within the interior volume. Together, this structure forms a therapeutic jewelry device.

In accordance with various embodiments, the therapeutic fluid may be a thermal adjustment therapeutic fluid. For example, the thermal adjustment therapeutic fluid may include a property or benefit that provides at least one of a heating or cooling property. In various embodiments, the therapeutic fluid may be a refrigerant fluid. The refrigerant may be a gel or liquid. The refrigerant may be a reusable refrigerant. The refrigerant may be at least one of diethylene glycol, ethylene glycol, hydroxythylcellulose or vinyl-coated silica gel.

In accordance with various embodiments, the stringing member may be an elongated, flexible member with engageable ends to form a loop. The stringing member may be a string, a chain, or a band. The jewelry device may include a plurality of the filled jewelry body elements with sealed caps strung along the stringing member. The plurality of the filled jewelry body elements are arranged on the stringing member as a necklace to provide therapeutic treatment about a user's neck. The plurality of the filled jewelry body elements may be arranged on the stringing member as a bracelet to provide therapeutic treatment about a user's wrist.

In accordance with various embodiments, a therapeutic jewelry device may be formed by providing a first container portion and a second container portion. The first container portion may be sealed to the second container portion together thereby forming a jewelry body element having an interior cavity. A filling opening may be provided in at least one of the first container portion or the second container portion. The filling opening may extend into the interior cavity. The interior cavity may be filled with a therapeutic fluid through the filling opening. The filling opening may be plugged with a cap. Formation of the jewelry device may include inserting a stringing member through an aperture that extends through at least one of the first container portion or the second container portion. When the cap plugs the filling opening, the aperture may be sealed off from the interior cavity such that it does not open into the interior cavity. A plurality of jewelry body elements may be strung together to form a therapeutic jewelry device.

BRIEF DESCRIPTION OF THE DRAWINGS

FIG. 4 depicts an isometric view of a container portion, in accordance with an embodiment of the present invention;

FIG. 5 depicts an isometric view of a different container portion, in accordance with an embodiment of the present invention;

FIG. 6 depicts an isometric view of a cap, in accordance with an embodiment of the present invention.

DETAILED DESCRIPTION

Disclosed herein are various embodiments of a therapeutic jewelry device. The therapeutic jewelry provided may provide a therapeutic heating or cooling effect to a user. This may be accomplished by the formation of a heating or cooling device that the user can wear. For example, the wearable item is jewelry such as a bracelet or necklace. The therapeutic jewelry may include a stringing member, a first therapeutic container portion, a second therapeutic container portion, and a cap. The first therapeutic container portion may define a first internal cavity, which includes a receiving member extending across, and has a hollow interior open at opposite sides of the first therapeutic portion to receive the thread there through. The second therapeutic container portion defines a second internal cavity. The second therapeutic container portion may be connectable to the first container portion forming a jewelry element body. The first and second internal cavities may cooperatively form an interior fluid cavity. At least one of the first or second container portions may define a filling aperture open to the interior fluid cavity of the jewelry element body, enabling filling the interior fluid cavity. The cap is operably connectable to seal the filling opening so that the interior fluid cavity is sealed to fluid therein while maintaining the opening of the hollow interior of the receiving member open to receive the stringing member.

Figure 1:
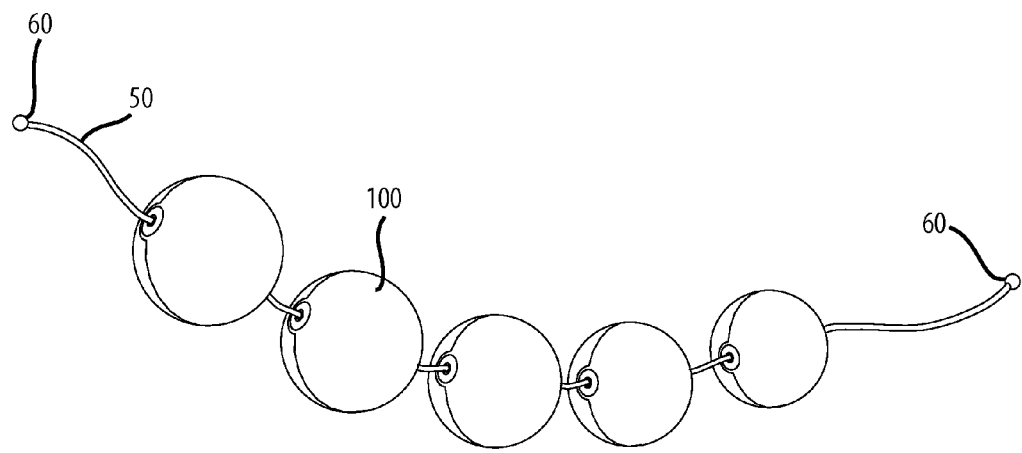
FIG. 1 depicts an isometric view of a therapeutic jewelry device, in accordance with an embodiment of the present invention.

Referring to FIG. 1, a therapeutic jewelry device 10 may include one or more jewelry body elements 100. The one or more jewelry body elements 100 may be held along a stringing member 50. In embodiments with a plurality of jewelry body elements 100, the plurality of jewelry body elements 10 may be strung along the length of the stringing member 50. The jewelry body elements 100 may be strung along the thread continuously, i.e. with one jewelry body element 100 in contact with the next; the jewelry body elements 100 may be strung along the thread discontinuously, i.e. with one jewelry body element 100 spaced away from the next, or the jewelry body elements 100 may be strung along the thread in a changing pattern or randomly.

In accordance with various embodiments, the stringing member 50 may be an element or device operable to support one or more of the body elements 100. The stringing member 50 may also be operable to suspend a plurality of body elements 100 in relation to one another. The stringing member 50 may be an elongated, flexible member with engageable ends 60 that are operable to form a loop. The loop may allow the stringing member 50 to suspend the one or more body elements 100 around an appendage of a user. The stringing member 50 may be any form of thread such as a string, a chain, band, or the like; or the stringing member 50 may be separate connecting portions that are individually attached to each of the body elements 100, which may allow the body elements 100 to form a chain. The engageable ends 60 may be any mechanism operable to connect one end of the stringing member 50 to another end of the stringing member 50. Examples may include locks, clasps, hooks, or the like extending from the end of stringing member 50.

In various embodiments, the jewelry device 10 may include a plurality of the filled jewelry body elements 100 with sealed caps strung along the stringing member 50. The plurality of the filled jewelry body elements are arranged on the stringing member 50 as a piece of jewelry. For example, the jewelry may be a necklace that provides therapeutic treatment about a user's neck. In another example, the jewelry may be a bracelet that provides therapeutic treatment about a user's wrist, ankle or other body part. The plurality of the filled jewelry body elements may be arranged on the stringing member as a bracelet to provide therapeutic treatment about a user's wrist. The filled jewelry body elements may range in size from ½ inch to 2 inches. In some embodiments, they may be less than the ½ inch or more than the 2 inches. The various jewelry device 10 assemblies may range in length from 8 inches to 24 inches. In some embodiments, they may be less than the ½ inch or more than the 2 inches.

A discussed in more detail herein, the jewelry body element 100 may be formed in multiple portions. In various embodiments, the jewelry body elements 100 may be formed from any material suitable to contain a therapeutic fluid including for example, polymers, metals, composites, or the like. After assembly of the components, the seams of the components may be smoothed to present a continues surface better conforming to the surface of known jewelry such as pearls. The surfaces may also be treated to conform aesthetically to the desired jewelry type such as pearls. For example the surfaces may be painted or have a similar treatment performed.

Figure 2:
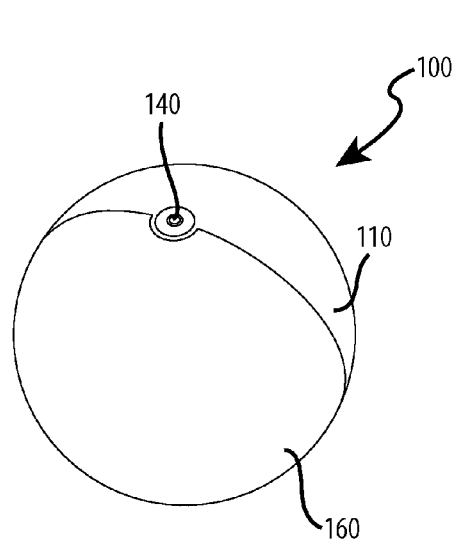
FIG. 2 depicts a bottom isometric view of a jewelry body element, in accordance with an embodiment of the present invention.

Referring to FIG. 2, which depicts a bottom isometric view of a jewelry body element, each jewelry body element 100 may include one or more container portions. In accordance with various embodiments, the jewelry body element 100 may include multiple elements such as container portion 110 and/or container portion 160. The container portions 110, 160 may form a container that is operable to hold a fluid in its interior. The jewelry body elements 100 may be formed such they are stringable together with one another. The jewelry body elements 100 may be strung with one or more stringing elements (e.g. element 50).

Figure 3:
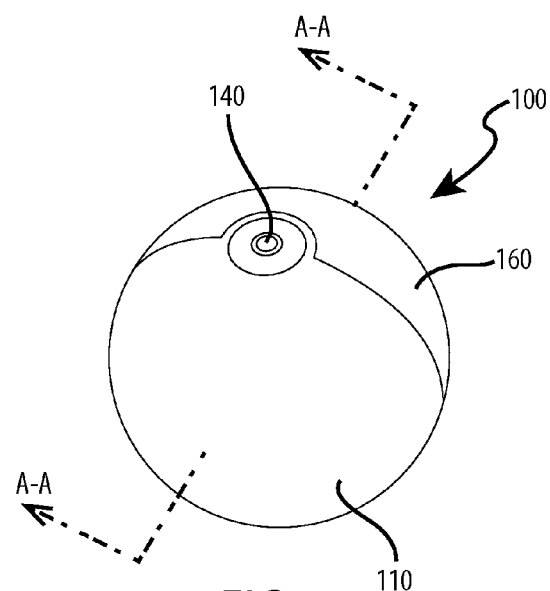
FIG. 3 depicts a top isometric view of a jewelry body element, in accordance with an embodiment of the present invention.

As shown in FIG. 3, which depicts a top isometric view of a jewelry body element, the jewelry body element 100 may further include a cap 150 that encloses an opening suitable to fill the jewelry body element 100 with a therapeutic fluid. In accordance with various embodiments, the opening may be located at any location suitable to receive the therapeutic fluid from the exterior of the jewelry body element 100 and pass it into the interior. The cap 150 may be sized to fit within the opening and close the opening, limiting the ability of the internal contents of the jewelry body element 100 to escape from within the jewelry body element 100. In various embodiments, the cap 150 may be permanently affixed to the jewelry body element 100. For example, the cap 150 may be attached to the jewelry body element 100 through any known attachments. Examples of such attachments may include a mechanical press fit, an adhesive attachment, a welded attachment between features, or similar processes or methods. Alternatively, in other embodiments, the cap 150 may be removably attached to the jewelry body element 100 via a removable engagement such as a snap fit, threadable engagement, or the like.

As shown in FIGS. 2-3, the jewelry body element 100 may also include a receiving member 140. The receiving member 140 may be defined by an aperture extending from one side of the jewelry body element 100 to the other side. The receiving member 140 may be entirely defined by one container portion such as each one of container portions 110 or 160; or the receiving member 140 may be defined by both the container portions 110 or 160. In various embodiments, the receiving member 140 may be a tubular channel.

In accordance with various embodiments, the jewelry body element 100 may have any shape. The shapes may include geometric shapes such as spheres, blocks, cones, frustums, pyramids, or the like. Alternatively, the shapes may include specialty formed shapes such as characters, crosses, rings, or any other known cosmetic-actuating design. In accordance with various embodiments and referring to FIGS. 2-5, the therapeutic container portion 110 and the therapeutic container portion 160 may be individual hemispheres that when connected together form a sphere. Once the two hemispheres are connected together forming a sphere, it may be operable as a container that may contain the therapeutic fluid 200. After the container portion 110 and the container portion 160 are connected together, they may be filled with a therapeutic fluid 200. The cap 150 may be inserted to plug the opening used to fill the containers 110, 160. This may allow the cap 150 to enclose the therapeutic fluid within the interior volume. Together, this structure forms a therapeutic jewelry device 100.

In accordance with various embodiments, the therapeutic fluid 200 (as shown for example in FIG. 7) may include at least one of a heating or cooling property. For example, the therapeutic fluid 200 may be a refrigerant fluid operable to provide therapeutic cooling relief to a user. Alternatively, the therapeutic fluid 200 may be a fluid suitable to provide a therapeutic heating relief to a user. As used herein, refrigerant does not refer to a substance used in a refrigeration cycle but instead one that is suitable to be dropped to a cold temperature (e.g. below 0 degrees Celsius) and then absorb surrounding heat, thereby providing cooling effect to the substance's surroundings. In various examples, the refrigerant may be a gel or liquid. In various embodiments, the fluid may be a reusable fluid, i.e. one that after use can be cooled off again to offer the same therapeutic benefit as the first use. As an example, the fluid may be at least one of diethylene glycol, ethylene glycol, hydroxythylcellulose or vinyl-coated silica gel. In some embodiments, the fluid may be a one-time use fluid that reaches its low temperature through a chemical reaction. Once the reaction is complete and the refrigerant is brought up to room temperature, it does not provide the same function again. Other examples of the fluids used herein may include water or various gases operable to provide a therapeutic cooling benefit.

Referring to FIG. 4, which depicts an isometric view of an example of the container portion 160, the container portion 160 may be defined by a shell 180. The shell 180 may have an external surface 184 and an internal surface 176. The internal surface 176 may define an internal cavity 192 of the container portion. The container portion 160 may include a mating surface 172, 182. In various embodiments, the container portion 160 may include an engagement feature 183. The engagement feature may include any mechanical feature operable to align, mate, or engage an opposing container portion (e.g. container portion 110). For example, the engagement feature may be one that removably connects the portions such as a threadable engagement or a snap fit engagement. In another example, the engagement feature may be one that aligns the portions for a permanent engagement via an adhesive or plastic welding. As shown in FIG. 4, the engagement feature may be a groove 183 that is operable to receive a protrusion from an opposing container portion (e.g. container portion 110). The groove 183 may be defined by a channel that follows the profile of the shell 180. This channel may include a bottom mating surface 185 bordered by walls 186, 174 that extend from the surface 185 up to mating surfaces 182, 172, respectively.

Referring to FIG. 5, which depicts an isometric view of an example of a container portion 110, the container portion 110 may be defined by a shell 114. The shell 114 may have an external surface 117 and an internal surface 119. The internal surface 119 may define an internal cavity 196 of the container portion 110. The container portion 110 may include a mating surface 115, 116. In various embodiments, the container portion 110 may include an engagement feature 112. The engagement feature 112 may include any mechanical feature operable to align, mate, or engage an opposing container portion (e.g. container portion 160). For example, the engagement feature may be one that removably connects the portions, such as a threadable engagement or a snap fit engagement. In another example, the engagement feature may be one that aligns the portions for a permanent engagement via an adhesive and/or plastic welding such as ultrasonic welding. As shown in FIG. 5, the engagement feature may be a protrusion 112 that is operable to be inserted into a groove on an opposing container portion (e.g. container portion 160). The protrusion 112 may follow the profile of the shell 114. This protrusion 112 may include a mating surface 118 bordered by walls 111, 113 that extend from the surface 118 to the mating surfaces 115, 116, respectively.

Figure 7:
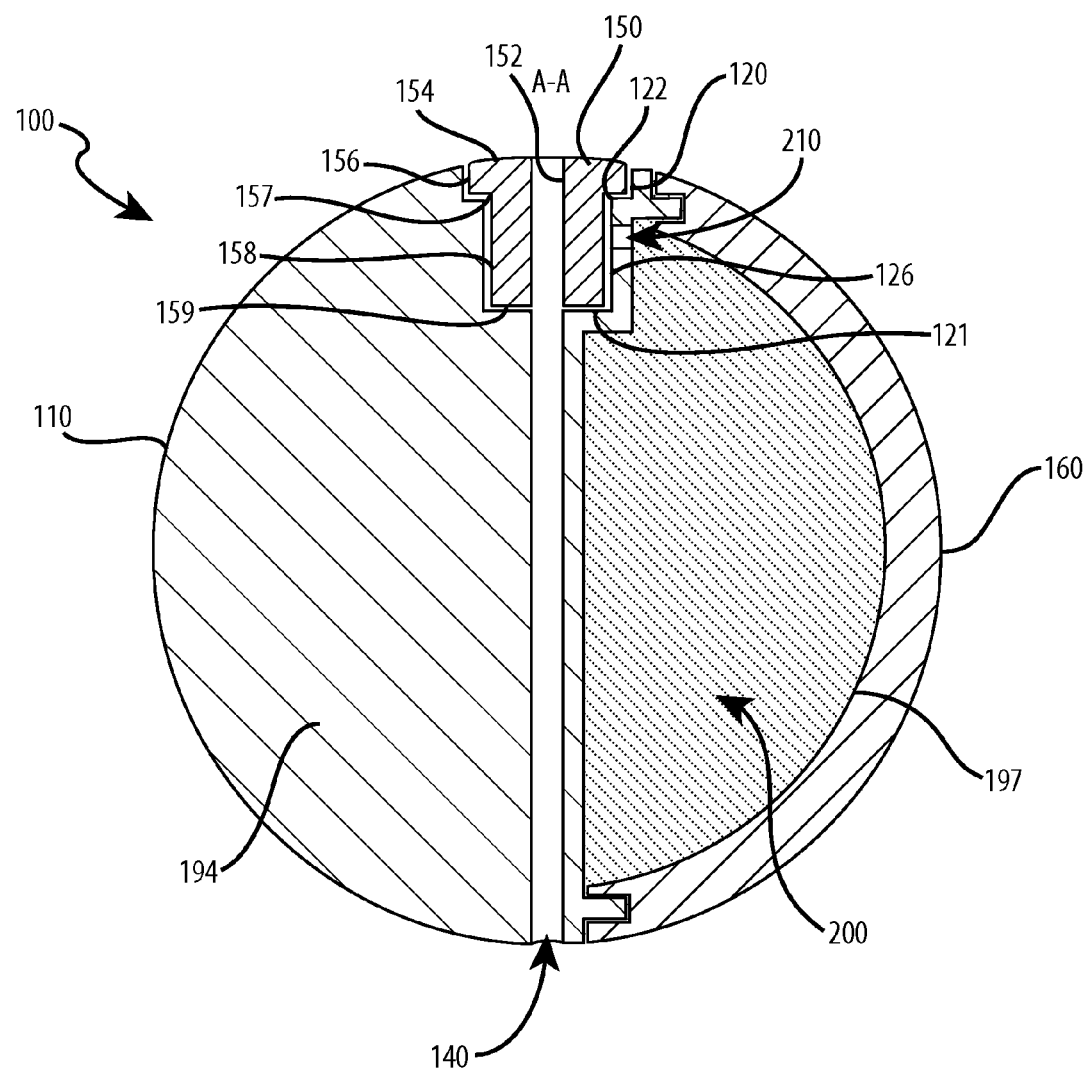
FIG. 7 depicts a cross-section view of the jewelry body element of FIG. 3 taken along cross-section line A-A, in accordance with an embodiment of the present invention.

In accordance with various embodiments and illustrated in FIGS. 5 and 7, the container portion 110 may include the receiving member 140. The receiving member 140 may be a hollow portion internal to the container portion 110 that is separate from the internal cavity (e.g. 194, 196). As indicated above, the receiving member 140 may be an aperture that extends from one side of the container portion 110 to the other. For example, a wall 130 may extend across the container portion 110. The wall 130 may define an outer shell of receiving member 140. The wall 130 may be connected to the internal surface 119 via a connection wall 132. The connection wall 132 may partition the internal cavity of the container portion 110 into two cavities 196, 194. The openings at each end of the receiving member 140 may be the same size. In this way, the cross section of the aperture forming the receiving member 140 may be generally constant. In other embodiments, as discussed below, the openings at each end of the receiving member 140 may be different size. In this way the, the cross section of the aperture forming the receiving member 140 may be variable.

The hollow interior portion of the receiving member 140 may include an enlarged portion 124 proximal to one of its ends. For example, at one end of the aperture forming the receiving member 140 the opening may have a larger axial radius than the remainder of the receiving member 140. The larger axial radius may enable a larger amount of fluid to flow through the enlarged portion as compared to the remainder of the receiving member 140 having a smaller cross-section. The enlarged portion 124 may be operable to receive the cap 150. The enlarged portion may be defined by a wall 126. The surface may be any shape, but, as one example, it may be cylindrical. The wall 126 may conform to a similar exterior surface on the cap 150 such the two surfaces are operable to form a seal. In various embodiments, the enlarged portion 124 may include one or more steps operable to control the depth to which the cap 150 or another item enters into the enlarged portion 124. One step may be defined by a mating surface 122 and an extension surface 120 extending therefrom. The mating surface 122 may be located just below the external surface 117 of the container portion 110 with the extension surface extending from the mating surface 122 to the external surface 117. Another step may be defined by a mating surface 121 and wall 126. The mating surface 121 may be located farther from the external surface than the mating surface 122. Wall 126 may connect mating surface 121 to mating surface 122.

In accordance with various embodiments, the receiving member 100 may be contained in only one container portion (e.g. container portion 110) as such the cap 150 may be inserted and contained in just the single container portion without direct association with the other container portion (e.g. container portion 160). This design may simplify the structure and manufacturing costs of one of the container portions reducing manufacturing costs. However in other embodiments, the cap 150 may be directly associated with more than one container portion.

As indicated above, in various embodiments the container portions may each be hemispherical. Thus container portion 110 may be hemispherical. The mating surfaces 115, 116 may be hemispherical mating surfaces that mate with hemispherical mating surfaces 182, 172 of the container portion 160. The receiving member 140 may be centered on a hemispherical surface of the second therapeutic container portion. Once the two hemispherical portions are assembled forming a sphere, the cap may be inserted into the receiving member along the same hemispherical plane. In embodiments having the enlarged portion 124, the enlarged portion 124 may be likewise aligned with the receiving member 140 at this hemispherical plane defined by the hemispherical surfaces. The therapeutic container portion 110 engagement portion may be a tongue 112 that extends from the hemispherical surface for engagement with the groove 183 of therapeutic container portion 160. The groove 183 of the therapeutic container portion 160 may extend into the hemispherical surfaces 182,172.

In accordance with various embodiments, the receiving portion 140 may include a filling aperture 210. The filling aperture 210 may be located within the hollow interior of the receiving member 140 so that the interior fluid cavity is fillable through the hollow interior. The filling aperture 210 may be any shape suitable to pass a therapeutic fluid there through, such as a generally radial, a generally rectangular passage, or similar. In various embodiments, the filling aperture may be disposed in the enlarged portion 124. The enlarged portion may be operable to receive the cap 150 in such a way that the cap 150 plugs the filling aperture 210 located within the enlarged portion. The exterior housing of the enlarged portion, formed around the filling aperture 210, may be structured such that it may be formed by a pull from a plastic injection molding tool. For example, the housing may have a flat side wall 216 extending toward the connecting wall 132. The surface proximal to the filling aperture 210 may be curved.

As the receiving member 140 may be housed entirely in one half of the jewelry body element 100, and also be aligned with a plane that is defined by the mating surface of the two halves, a protruding engagement feature may extend around the receiving member 140. For example, container portion 110 may include a surface 125, 127 that protrudes from the mating surfaces 115, 116 and extends around the receiving member 140. The container portion 160 may have recess surfaces 173, 175, which are operable to receive the surfaces 125, 127. Similar mating surfaces such as 188, 174, 189, and 179 may be present on container portion 160.

The first therapeutic container portion, the second therapeutic container portion, or the cap may be plastic welded or adhered to one another. The cap 150 may include a central through hole aligned with the hollow interior to receive the stringing member.

Referring to FIG. 6, which depicts an isometric view of the cap 150 in accordance with various embodiments, the cap 150 may configured to be inserted into the receiving member 140. The cap 150 may include a top surface 154. The top surface 154 may have a shape that generally conforms to the shape of the outer surface of the jewelry body element 100. For example, in embodiments in which the jewelry body element 100 is a sphere then the top surface 154 may include a surface that would conform to the spherical profile of the jewelry body element 100. Thus, in response to the cap 150 being plunged into the receiving element 140, the top surface 154 may align with the outer surface of the jewelry body element 100 forming a continuation of that surface. As shown in FIGS. 6 and 7, the cap 150 may include a mating wall 158 operable to be inserted into the receiving member 140 and mate with the enlarged portion 124. The cap may have a bottom surface 159 and, in various embodiments, it may also include a stepped surface 157. One of the bottom surfaces 159 or the stepped surface 157 may be positioned to engage surface 121 or 122 respectively. Surface 156 may extend between stepped surface 157 and the top surface 154. A through hole defined by interior surface 152 may extend through cap 150. A lead-in 153 may be located at the intersection of top surface 154 and interior surface 152 to provide an easy path to thread a stringing member 50 through the cap 150 and into the receiving member 140.

As shown in FIG. 7, the therapeutic fluid 200 may at least partially fill the interior cavity 197. In various embodiments, the therapeutic fluid 200 may fill the interior cavity 197 at least up to the filling aperture 210. The position of the filling aperture may be located anywhere along the height of receiving member 140; or, in embodiments including the enlarged portion, the filling aperture may be located anywhere along the height of the enlarged portion 120. In various examples, this fill may be greater than 50% of the interior cavity. In various examples, this fill may be greater than 75% of the interior cavity. In various examples, this fill may be greater than 90% of the interior cavity. The fluid may also be filled above the height of the filling aperture 210 by compensating for some drainage down the receiving member 140. Although FIG. 7 shows a cross-section through the wall 194, it may be noted that the interior cavity 197 extends into both container portions including container portion 110. Thus container portion 110 also includes fill from the therapeutic fluid 200. In various embodiments, substantially all of the interior volume of the interior cavity of the assembled container portions 110, 160 may be filled.

In accordance with various embodiments, a therapeutic jewelry device may be formed by providing a first container portion and a second container portion. The first container portion may be sealed to the second container portion thereby forming a jewelry body element having an interior cavity. The sealing may be performed by an adhesive suitable selected based on the material being sealed as would be understood by a person of ordinary skill in the art. However, the seal may be formed by any substances, mechanism, or process. After sealing the container portions may receive a secondary sealing process. For example, the container portions may be sealed with an ultrasonic welding process. Once assembled the jewelry body element may receive cosmetic post processing. For example, the connection between the two container portions may then be sanded to provide a consistent surface across the connection line. The container portions may also have a cosmetic coating applied to give the container portions the appearance of any of a variety of cosmetic accessories, such as pearls. The cosmetic coating may for example include paint such as a lacquer, intense nail polish. Specific colors may be selected to give the appearance of a particular accessory such as pearlescent white giving the connected container portions the appearance of a peal. In some embodiments the color can be molded into the material. Before, after, or instead of the cosmetic post processing, a filling opening may be provided in at least one of the first container portion or the second container portion. The filling opening may extend into the interior cavity. The interior cavity may be filled with a therapeutic fluid through the filling opening. The filling opening may be plugged with a cap. Formation of the jewelry device may include inserting a stringing member through an aperture that extends through at least one of the first container portion or the second container portion. When the cap plugs the filling opening, the aperture may be sealed off from the interior cavity such that it does not open into the interior cavity. A plurality of jewelry body elements may be strung together to form a therapeutic jewelry device.

Having described several embodiments herein, it will be recognized by those skilled in the art that various modifications, alternative constructions, and equivalents may be used. The various examples and embodiments may be employed separately or they may be mixed and matched in combination to form any iteration of the alternatives. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. Therapeutic jewelry comprising:
    a first therapeutic container portion forming a first internal cavity and including a receiving member extending across, and having a hollow interior open at opposite sides of the first therapeutic portion to define openings operable to receive a stringing member therethrough;
    a second therapeutic container portion forming a second internal cavity and connectable to the first container portion, to form a jewelry element body, such that the first and second internal cavities cooperatively form an interior fluid cavity;
    wherein at least one of the first or second container portions define a filling aperture open to the interior fluid cavity of the jewelry element body, enabling filling the interior fluid cavity; and
    a cap having an interior surface thereof defining an opening operable to receive the stringing member therethrough, the cap being operably connectable to seal the filling aperture so that the interior fluid cavity is sealed to fluid therein, while maintaining the openings of the hollow interior of the receiving member open to be operable to receive the stringing member; wherein the receiving member is a tubular channel that extends across the first therapeutic container portion and the filling aperture is located within the hollow interior of the receiving member so that the interior fluid cavity is fillable through said hollow interior.

2. The therapeutic jewelry of claim 1, wherein the stringing member is inserted and extends through the receiving member.

3. The therapeutic jewelry of claim 1, wherein the filling aperture is at least one of a generally radial or a generally rectangular passage to the interior fluid cavity.

4. The therapeutic jewelry of claim 1, wherein the first therapeutic container portion, the second therapeutic container portion, or the cap is plastic welded or adhered to one another.

5. The therapeutic jewelry of claim 1, wherein the hollow interior has an enlarged portion near one of the openings with the filling aperture being disposed in the enlarged portion and the enlarged portion being operable to receive the cap such that the cap plugs the filling aperture located within the enlarged portion.

6. The therapeutic jewelry of claim 5, wherein the cap includes a cap through hole aligned with the hollow interior to receive a stringing member.

7. The therapeutic jewelry of claim 1, wherein the first therapeutic container portion and the second therapeutic container portion are individual hemispheres that when connected together form a sphere.

8. The therapeutic jewelry of claim 6, wherein the receiving member and the cap through hole are centered on a hemispherical surface of the second therapeutic container portion.

9. The therapeutic jewelry of claim 8, wherein the second therapeutic container portion includes a ridge extending from the hemispherical surface forming a tongue for engagement with the first therapeutic container portion.

10. The therapeutic jewelry of claim 9, wherein the first therapeutic container portion includes a groove extending into the hemispherical surface for receiving the tongue of the second therapeutic container and providing engagement therebetween.

11. The therapeutic jewelry of claim 1, wherein the first therapeutic container portion and the second therapeutic container portion are connected together and filled with a therapeutic fluid and the cap is inserted into the filling aperture enclosing the therapeutic fluid within the interior fluid cavity and this structure together forms a therapeutic jewelry device.

12. The therapeutic jewelry of claim 11, wherein the therapeutic fluid includes at least one of a heating or cooling property.

13. The therapeutic jewelry of claim 12, wherein the therapeutic fluid is a refrigerant fluid.

14. The therapeutic jewelry of claim 12, wherein the refrigerant is a gel or liquid.

15. The therapeutic jewelry of claim 13, wherein the refrigerant is a reusable refrigerant.

16. The therapeutic jewelry of claim 13, wherein the refrigerant is at least one of diethylene glycol, ethylene glycol, hydroxythylcellulose or vinyl-coated silica gel.

17. The therapeutic jewelry of claim 1, wherein the stringing member is an elongated, flexible member with engageable ends to form a loop.

18. The therapeutic jewelry of claim 1, wherein the stringing member is a string, chain, or band.

19. The therapeutic jewelry of claim 18, further comprising a plurality of additional, filled jewelry element bodies each having a corresponding sealed cap strung along the stringing member.

20. The therapeutic jewelry of claim 19, wherein the plurality of the additional, filled jewelry element bodies are arranged on the stringing member as a necklace to provide therapeutic treatment about a user's neck.

21. The therapeutic jewelry of claim 19, wherein the plurality of the additional, filled jewelry element bodies are arranged on the stringing member as a bracelet to provide therapeutic treatment about a user's wrist.

22. Method of providing a therapeutic treatment comprising
providing a first container portion and a second container portion, wherein the first container portion defines openings that are configured to operably receive a stringing member therethrough;
sealing the first container portion to the second container portion together thereby forming a jewelry body element having an interior cavity;
providing a filling opening in at least one of the first container portion or the second container portion that extends into the interior cavity;
filling the interior cavity with a therapeutic fluid through the filling opening; and
plugging the filling opening with a cap that has an interior surface that defines an opening operable to receive the stringing member therethrough; wherein filling the interior cavity with a therapeutic fluid through the filling opening includes flowing the therapeutic fluid through the openings that are configured to operably receive a stringing member therethrough.

23. The method of claim 22, further comprising inserting a stringing member through an aperture that extends through at least one of the first container portion or the second container portion and through the opening of the first container portion in the cap, wherein the aperture does not open into the interior cavity when the cap is plugged into the filling opening.

24. Therapeutic jewelry comprising:
a first therapeutic container portion forming a first internal cavity and including a receiving member extending across, and having a hollow interior open at opposite sides of the first therapeutic portion to define openings operable to receive a stringing member therethrough;
a second therapeutic container portion forming a second internal cavity and connectable to the first container portion, to form a jewelry element body, such that the first and second internal cavities cooperatively form an interior fluid cavity;
wherein at least one of the first or second container portions define a filling aperture open to the interior fluid cavity of the jewelry element body, enabling filling the interior fluid cavity; and
a cap having an interior surface thereof defining an opening operable to receive the stringing member therethrough, the cap being operably connectable to seal the filling aperture so that the interior fluid cavity is sealed to fluid therein, while maintaining the openings of the hollow interior of the receiving member open to be operable to receive the stringing member; wherein the first therapeutic container portion and the second therapeutic container portion are individual hemispheres that when connected together form a sphere.

* * * * *